US010647643B2

(12) United States Patent
Hodgson et al.

(10) Patent No.: US 10,647,643 B2
(45) Date of Patent: May 12, 2020

(54) PROCESS FOR DRYING HYDRO(CHLORO)FLUOROOLEFINS

(71) Applicant: MEXICHEM FLUOR S.A. DE C.V., San Luis Potosi (MX)

(72) Inventors: Emma Jayne Hodgson, Cheshire (GB); James Henry Murray, Cheshire (GB); Gary Lloyd, Cheshire (GB)

(73) Assignee: MEXICHEM FLUOR S.A. DE C.V., San Luis Potosi (MX)

( * ) Notice: Subject to any disclaimer, the term of this patent is extended or adjusted under 35 U.S.C. 154(b) by 0 days.

(21) Appl. No.: 15/745,489

(22) PCT Filed: Jul. 14, 2016

(86) PCT No.: PCT/GB2016/052144
§ 371 (c)(1),
(2) Date: Jan. 17, 2018

(87) PCT Pub. No.: WO2017/013405
PCT Pub. Date: Jan. 26, 2017

(65) Prior Publication Data
US 2018/0215691 A1 Aug. 2, 2018

(30) Foreign Application Priority Data

Jul. 17, 2015 (GB) .................................. 1512510.7

(51) Int. Cl.
*C07C 17/38* (2006.01)

(52) U.S. Cl.
CPC .................................. *C07C 17/38* (2013.01)

(58) Field of Classification Search
CPC ....... C07C 17/087; C07C 17/21; C07C 17/25; C07C 17/38; C07C 17/383; C07C 17/206; C07C 19/10
See application file for complete search history.

(56) References Cited

U.S. PATENT DOCUMENTS

2005/0013764 A1   1/2005   Merkel et al.
2012/0184785 A1   7/2012   Cottrell

FOREIGN PATENT DOCUMENTS

CN        203346305       12/2013
GB          2143526        2/1985
WO      WO2014/159009     10/2014

OTHER PUBLICATIONS

International Search Report pertaining to PCT/GB2016/052144, dated Oct. 26, 2016, 3 pages.

*Primary Examiner* — Jafar F Parsa
(74) *Attorney, Agent, or Firm* — Ryan Kromholz & Manion, S.C.

(57) ABSTRACT

The present invention provides a method for purifying a fluid comprising a first drying stage which comprises contacting a first fluid stream comprising one or more hydro(chloro)fluoroolefins and water with a source of sulphuric acid to produce a first treated fluid stream comprising the hydro(chloro)fluoroolefin(s) and a first spent sulphuric acid stream, wherein the first treated fluid stream comprises a lower concentration of water than the first fluid stream.

52 Claims, 4 Drawing Sheets

PROCESS FOR DRYING HYDRO(CHLORO)FLUOROOLEFINS

The present invention relates to processes useful in the production of hydro(chloro)fluoroolefins, for example in relation to the cleaning and/or purification of intermediate and product streams. In particular, the invention provides methods for cleaning and/or purifying product streams comprising fluoropropenes such as 1,3,3,3-tetrafluoropropene (HFO-1234ze) and 2,3,3,3-tetrafluoropropene (HFO-1234yf).

(Hydro)halocarbons are typically used as refrigerant or propellant materials and as blowing agents. Over the last 20 years, the variety of (hydro)halocarbons used in these applications has changed as it has been discovered that some such materials (such as difluorodichloromethane, R12) deplete the earth's ozone layer, while others (such as 1,1,1,2-tetrafluoroethane, R134a) have an unacceptably high action as a greenhouse gas.

Hydro(chloro)fluoroolefins have emerged as a class of compounds which may address these problems by providing good performance as refrigerants, propellant materials and as blowing agents, while also having a low ozone depletion potential and a low global warming potential.

Various methods have been proposed for the production of hydro(chloro)fluoroolefins. Such methods require the removal of unused reagents and reaction by-products before the resulting product is in a condition fit for sale. Scrubbing techniques which have previously been used in the production of hydrofluorocarbon compounds have been found to degrade the hydro(chloro)fluoroolefin products such that the number and quantity of by-products is increased and the overall product yield falls.

Accordingly, there is a need for a process of cleaning and/or purifying a hydro(chloro)fluoroolefin product stream which is both effective and provides for a minimal degradation of the relevant product, which reduces product yield and may create waste streams which contain hazardous materials and/or are difficult or expensive to dispose of. The present invention provides such a process.

There is also a need for an efficient method for removing unwanted water from a hydro(chloro)fluoroolefin product stream as, for example, methods of cleaning and/or purifying the product stream may introduce water to the product stream. The present invention provides such a process.

In a first aspect, the present invention provides a method comprising a first drying stage which comprises contacting a first fluid stream comprising one or more hydro(chloro)fluoroolefins and water with a source of sulphuric acid to produce a first treated fluid stream comprising the hydro(chloro)fluoroolefin(s) and a first spent sulphuric acid stream, wherein the first treated fluid stream comprises a lower concentration of water than the first fluid stream.

Preferably, the first treated fluid stream comprises less than 1 wt % water, for example less than about 500 ppm water. More preferably, the first treated fluid stream contains less than about 250 ppm water, less than 100 ppm water or less than 10 ppm water.

Preferably, the first fluid stream comprises less than about 20 wt % HF, for example less than 10 wt % HF, less than 5 wt % HF or less than 1 wt % HF. In some embodiments the first fluid stream comprises no more than trace quantities of HF.

Preferably, the first fluid stream comprises less than about 20 wt % HCl, for example less than 10 wt % HCl, less than 5 wt % HCl or less than 1 wt % HCl. In some embodiments the first fluid stream comprises no more than trace quantities of HCl.

Preferably the first drying stage is performed in a first sulphuric scrubbing vessel. Preferably, the residence time of the first fluid stream in the first scrubbing vessel is between about 1 s and about 60 s. Preferably, the residence time of the first source of sulphuric acid in the first sulphuric scrubbing vessel is between about 5 s and 10000 s.

Preferably, at least 50 wt % of the first fluid stream comprises the hydro(chloro)fluoroolefin(s). More preferably, at least 60 wt %, 70 wt % or 80 wt % of the first fluid stream comprises hydro(chloro)fluoroolefin(s). In certain preferred embodiments, at least 50 wt % of the first fluid stream comprises one hydro(chloro)fluoroolefin. More preferably, at least 60 wt %, 70 wt % or 80 wt % of the first fluid stream comprises one hydro(chloro)fluoroolefin.

In some preferred embodiments, at least 50 wt % of the first fluid stream comprises a hydro(chloro)fluoroolefin selected from the group hydrofluoropropenes, hydrochlorofluoropropenes, hydrofluoroethylenes, hydrofluorobutenes and hydrochlorofluorobutenes. More preferably, at least 60 wt %, 70 wt % or 80 wt % of the first fluid stream comprises a hydro(chloro)fluoroolefin selected from the group hydrofluoropropenes, hydrochlorofluoropropenes, hydrofluoroethylenes, hydrofluorobutenes and hydrochlorofluorobutenes. Preferred hydro(chloro)fluoroolefins include HFO-1234yf, HFO-1234ze, 1-chloro-3,3,3-trifluoropropene (HCFO-1233zd), 2-chloro-3,3,3-trifluoropropene (HCFO-1233xf), 1,1,1-4,4,4-hexafluoro-but-2-ene (HFO-1336mzz) and 1,1-difluoroethylene (HFO-1132a).

In preferred embodiments, the first source of sulphuric acid comprises aqueous sulphuric acid at a concentration between around 60 wt % and around 98 wt %. More preferably, the first source of sulphuric acid comprises aqueous sulphuric acid at a concentration between around 75 wt % and around 95 wt %, for example between around 78 wt % and about 94 wt %. In certain embodiments, the first source of sulphuric acid comprises aqueous sulphuric acid at a concentration between about 78 wt % and about 90 wt %. The inventors have found that even small reductions in the concentration of the sulphuric acid as compared to concentrated sulphuric acid provide significant reductions in the degradation of the hydro(chloro)fluoroolefin(s), thereby providing greater final product yields and reducing the concentration of potentially hazardous organic material in the spent sulphuric acid stream.

It is preferred that the first fluid stream is in the vapour phase when contacted with the source of sulphuric acid. Preferably, the first fluid stream is contacted with the source of sulphuric acid at a temperature between about 10° C. and about 70° C., for example between about 20° C. and about 60° C. Most preferably, the first fluid stream is contacted with the source of sulphuric acid at a temperature between about 20° C. and 40° C., for example between about 25° C. and 35° C., e.g. around 30° C. It is preferred that the first fluid stream is contacted with the source of sulphuric acid at a sufficiently high temperature to minimise or prevent condensation of the hydro(chloro)fluoroolefin.

Preferably, the first spent sulphuric stream comprises less than about 20000 ppm fluoride, for example less than about 15000 ppm fluoride, e.g. less than about 10000 ppm fluoride, less than about 8000 ppm fluoride, less than about 5000 ppm fluoride, less than about 4000 ppm fluoride, less than about 3000 ppm fluoride or less than about 2000 ppm fluoride. In some embodiments, the first spent sulphuric stream comprises less than about 1000 ppm fluoride, for example less than about 500 ppm fluoride. In most preferred embodiments, the first spent sulphuric stream comprises less than about 100 ppm fluoride, for example less than about 80 ppm fluoride, less than about 50 ppm fluoride, less than about 40 ppm fluoride or less than about 25 ppm fluoride.

In preferred embodiments, the first spent sulphuric stream comprises less than about 10000 ppm total organic carbon. For example, in some embodiments, the first spent sulphuric stream comprises less than about 8000 ppm total organic carbon, less than about 5000 ppm total organic carbon, less than about 4000 ppm total organic carbon, less than about 3000 ppm total organic carbon or less than about 2000 ppm total organic carbon. In some embodiments, the first spent sulphuric stream comprises less than about 1000 ppm total organic carbon. In most preferred embodiments, the first spent sulphuric stream comprises less than about 500 ppm total organic carbon, for example less than about 250 ppm total organic carbon, less than about 100 ppm total organic carbon, less than about 50 ppm total organic carbon or less than about 25 ppm total organic carbon.

In some embodiments, the method comprises a second drying step comprising contacting the first treated fluid stream with a second source of sulphuric acid to produce a second treated fluid stream comprising the hydro(chloro)fluoroolefin(s) and a second spent sulphuric acid stream, wherein the second treated fluid stream comprises a lower concentration of water than the first treated fluid stream. In such an embodiment it is preferred, though not essential, that the first source of sulphuric acid comprises aqueous sulphuric acid in a concentration between about 78 wt % and about 90 wt %.

The inventors have found that providing a second drying step, it is possible to perform the first drying step under milder conditions, allowing for the removal of significant quantities of water from the first fluid stream while minimising reaction with the hydro(chloro)fluoroolefin(s).

Preferably the second drying stage is performed in a second sulphuric scrubbing vessel. Preferably, the residence time of the first treated fluid stream in the second scrubbing vessel is between about 1 s and about 60 s. Preferably, the residence time of the second source of sulphuric acid in the second sulphuric scrubbing vessel is between about 5 s and 10000 s. Where a second drying step is included, it is preferred that the residence time of the first source of sulphuric acid in the first sulphuric scrubbing vessel is between about 5 s and 500 s.

Preferably, the second treated fluid stream comprises less than about 500 ppm water. More preferably, the second treated fluid stream contains less than about 250 ppm water, less than 100 ppm water or less than 10 ppm water.

In preferred embodiments, the second source of sulphuric acid comprises aqueous sulphuric acid at a concentration between around 60 wt % and around 98 wt %. More preferably, the second source of sulphuric acid comprises aqueous sulphuric acid at a concentration between around 75 wt % and around 95 wt %, for example between around 78 wt % and about 94 wt %. In certain embodiments, the second source of sulphuric acid comprises aqueous sulphuric acid at a concentration between about 90 wt % and about 94 wt %.

It is preferred that the first treated fluid stream is in the vapour phase when contacted with the second source of sulphuric acid. Preferably, the first fluid stream is contacted with the source of sulphuric acid at a temperature between about 10° C. and about 70° C., for example between about 20° C. and about 60° C. Most preferably, the first treated fluid stream is contacted with the second source of sulphuric acid at a temperature between about 20° C. and 40° C., for example between about 25° C. and 35° C., e.g. around 30° C. It is preferred that the first fluid stream is contacted with the source of sulphuric acid at a sufficiently high temperature to minimise or prevent condensation of the hydro(chloro)fluoroolefin.

Preferably, the second spent sulphuric stream comprises less than about 20000 ppm fluoride, for example less than about 15000 ppm fluoride, e.g. less than about 10000 ppm fluoride, less than about 8000 ppm fluoride, less than about 5000 ppm fluoride, less than about 4000 ppm fluoride, less than about 3000 ppm fluoride or less than about 2000 ppm fluoride. In some embodiments, the second spent sulphuric stream comprises less than about 1000 ppm fluoride, for example less than about 500 ppm fluoride. In most preferred embodiments, the second spent sulphuric stream comprises less than about 100 ppm fluoride, for example less than about 80 ppm fluoride, less than about 50 ppm fluoride, less than about 40 ppm fluoride or less than about 25 ppm fluoride.

In preferred embodiments, the second spent sulphuric stream comprises less than about 10000 ppm total organic carbon. For example, in some embodiments, the second spent sulphuric stream comprises less than about 8000 ppm total organic carbon, less than about 5000 ppm total organic carbon, less than about 4000 ppm total organic carbon, less than about 3000 ppm total organic carbon or less than about 2000 ppm total organic carbon. In some embodiments, the second spent sulphuric stream comprises less than about 1000 ppm total organic carbon. In most preferred embodiments, the second spent sulphuric stream comprises less than about 500 ppm total organic carbon, for example less than about 250 ppm total organic carbon, less than about 100 ppm total organic carbon, less than about 50 ppm total organic carbon or less than about 25 ppm total organic carbon.

Preferably, the first and/or, if produced, second treated fluid stream(s) comprise the hydro(chloro)fluoroolefin(s) in a substantially pure state or as part of a mixture of hydro(chloro)fluoroolefins and/or other halogenated organic compounds.

In preferred embodiments, the first and/or, if produced, second treated fluid stream is contacted with an adsorbent material. The adsorbent material removes or reduces the concentration of one or more components selected from residual acid (e.g. residual HF and/or residual HCl), residual water and/or residual impurities such as residual organic impurities.

In some embodiments, the adsorbent material comprises soda lime. In other embodiments, the adsorbent material comprises one or more molecular sieves, for example one or more zeolites having pores sizes in the region of 2 Å to 10 Å, e.g. about 3 Å to about 6 Å.

In some embodiments, the second treated fluid stream, optionally having been contacted with the adsorbent material, is subjected to distillation to separate some or all of the remaining components, for example to provide a substantially pure product stream.

In certain preferred embodiments, the method comprises a preceding acid removal step. The acid removal step preferably comprises the treatment of a crude product stream to remove at least a portion of any HF and/or HCl in the crude product stream to provide the first fluid stream. Preferably, the crude product stream is the product stream of a dehydrohalogenation reaction (e.g. a dehydrofluorination and/or dehydrochlorination reaction). More preferably, the dehydrohalogenation reaction provides the one or more hydro(chloro)fluoroolefins. As such, the crude product stream may contain HF and/or HCl in a molar concentration of around 0.5 to 1.5 times (e.g. 0.8 to 1.2 times) the molar concentration of the hydro(chloro)fluoroolefin(s) in the crude product stream. The crude product stream may also comprise one or more (hydro)haloalkanes, which may represent by-products of the dehydrohalogenation reaction and/or one or more unreacted starting materials.

In one preferred embodiment, the acid removal step comprises contacting the crude product stream with water to produce a spent stream of aqueous acid (e.g. HF and/or HCl) and a treated product stream, the treated product stream having a lower acid concentration (e.g. a lower HF and/or HCl concentration) than the crude product stream.

In an alternative embodiment, the acid removal step comprises contacting the crude product stream with a source of aqueous acid, e.g. a source of aqueous HF and/or HCl to produce a spent stream of aqueous acid (e.g. HF and/or HCl) and a treated product stream, the treated product stream having a lower acid concentration (e.g. a lower HF and/or HCl concentration) than the crude product stream. Preferably, the source of aqueous acid comprises aqueous HF in a concentration of at least about 40 wt % or at least about 50 wt %. Most preferably, the source of aqueous acid comprises aqueous HF in a concentration between about 40 wt % and about 60 wt %. In an alternative embodiment, the source of aqueous acid comprises aqueous sulphuric acid, for example in a concentration less than about 98 wt %, e.g. less than about 95 wt % or less than about 90 wt %.

In certain embodiments, HF and/or HCl is recovered from the spent stream of aqueous acid, for example by flash separation and/or distillation.

In some embodiments, the treated product stream is provided directly to the first drying stage, for example in the form of the first fluid stream. In other embodiments, the treated product stream is subjected to one or more further treatment steps before being provided to the first drying stage.

Preferably, the treated product stream is subjected to a second acid removal step. The second acid removal step preferably comprises contacting the treated product stream with an aqueous alkali to produce a second treated product stream and a spent aqueous alkali stream, the second treated product stream having a lower acid concentration than the treated product stream. In preferred embodiments, the source of aqueous alkali comprises aqueous caustic, for example aqueous NaOH or KOH. Preferably the aqueous NaOH or KOH is provided at a concentration of less than about 20 wt %, for example less than about 15 wt %, less than about 10 wt % or less than about 5 wt %.

In some embodiments, the second treated product stream is provided directly to the first drying stage, for example in the form of the first fluid stream. In other embodiments, the second treated product stream is subjected to one or more further treatment steps before being provided to the first drying stage.

In a further aspect of the invention, there is provided an integrated process for producing one or more hydro(chloro)fluoroolefins comprising:
(i) dehydrohalogenating one or more hydro(chloro)fluoroalkanes to form a crude product stream;
(ii) subjecting the crude product stream to a first acid removal step comprising contacting the crude product stream with water or a source of aqueous acid to produce a treated product stream and a spent aqueous acid stream;
(iii) optionally subjecting the treated product stream to a second acid removal step comprising contacting the treated product stream with a source of aqueous alkali to produce a second treated product stream and a spent aqueous alkali stream;
(iv) subjecting the treated product stream or, if produced, the second treated product stream, in the form of a first fluid stream, to a first drying stage comprising contacting the first fluid stream with a source of sulphuric acid to produce a first treated fluid stream comprising the hydro(chloro)fluoroolefin(s) and a first spent sulphuric acid stream.

In a further aspect, the invention provides a method for removing acid from a crude product stream of a dehydrohalogenation reaction, the crude product stream containing one or more hydro(chloro)fluoroolefins, the method comprising:
(i) subjecting the crude product stream to a first acid removal step comprising contacting the crude product stream with water or a source of aqueous acid to produce a treated product stream and a spent aqueous acid stream;
(ii) optionally subjecting the treated product stream to a second acid removal step comprising contacting the treated product stream with a source of aqueous alkali to produce a second treated product stream and a spent aqueous alkali stream.

In some embodiments, the method comprises subjecting the treated product stream or, if produced, the second treated product stream, in the form of a first fluid stream, to a first drying stage comprising contacting the first fluid stream with a source of sulphuric acid to produce a first treated fluid stream comprising the hydro(chloro)fluoroolefin(s) and a first spent sulphuric acid stream.

In another aspect, the invention provides a spent scrubbing liquor comprising aqueous sulphuric acid in a concentration of less than around 98 wt % (for example less than around 95 wt %, 90 wt %, 85 wt %, 80 wt %, 75 wt %, 70 wt %, 65 wt %, 60 wt %, 55 wt % or 50 wt %) and at least one compound selected from fluoracrylic acid, polyfluoracrylic acid, formic acid and fluoroformaldehyde, and/or one or more unsaturated fluorine containing oligomers. Preferably, the spent scrubbing liquor comprises sulphuric acid in a concentration between 50 wt % and 98 wt %, for example between 75 wt % and 95 wt %, e.g. between 75 wt % and the or a concentration of sulphuric acid in a scrubbing step which produces the spent liquor.

Preferably, the spent liquor comprises less than about 20000 ppm fluoride, less than about 15000 ppm fluoride, less than about 10000 ppm fluoride, less than about 8000 ppm fluoride, less than about 5000 ppm fluoride, less than about 4000 ppm fluoride, less than about 3000 ppm fluoride, less than about 2000 ppm fluoride, less than about 1000 ppm fluoride, less than about 500 ppm fluoride, less than about 100 ppm fluoride, less than about 80 ppm fluoride, less than about 50 ppm fluoride, less than about 40 ppm fluoride or less than about 25 ppm fluoride.

Preferably, the spent liquor comprises less than about 10000 ppm total organic carbon, less than about 8000 ppm total organic carbon, less than about 5000 ppm total organic carbon, less than about 4000 ppm total organic carbon, less than about 3000 ppm total organic carbon or less than about 2000 ppm total organic carbon, less than about 1000 ppm total organic carbon, less than about 500 ppm total organic carbon, less than about 250 ppm total organic carbon, less than about 100 ppm total organic carbon, less than about 50 ppm total organic carbon or less than about 25 ppm total organic carbon.

In another aspect of the invention, there is provided the use of a spent scrubbing liquor as described above in the production of a regenerated scrubbing liquor comprising sulphuric acid having a concentration between around 60 wt % and around 98 wt % (for example 75 wt % and around 95 wt %, for example between around 78 wt % and about 94 wt % or between about 78 wt % and about 90 wt %) for use in a scrubbing method as described herein.

In another aspect, the invention provides for the use of a regenerated scrubbing liquor as described herein in a scrubbing method as described herein.

In other embodiments, the spent liquor may be processed to be neutralised and to remove at least partially any fluoride and or organic compounds to allow for safe disposal.

As will be understood by the skilled person, any of the preferred and alternative embodiments presented above may be applicable to any of the described aspects of the invention.

Embodiments of the present invention will now be described with reference to the following examples and drawings.

Figure 1:
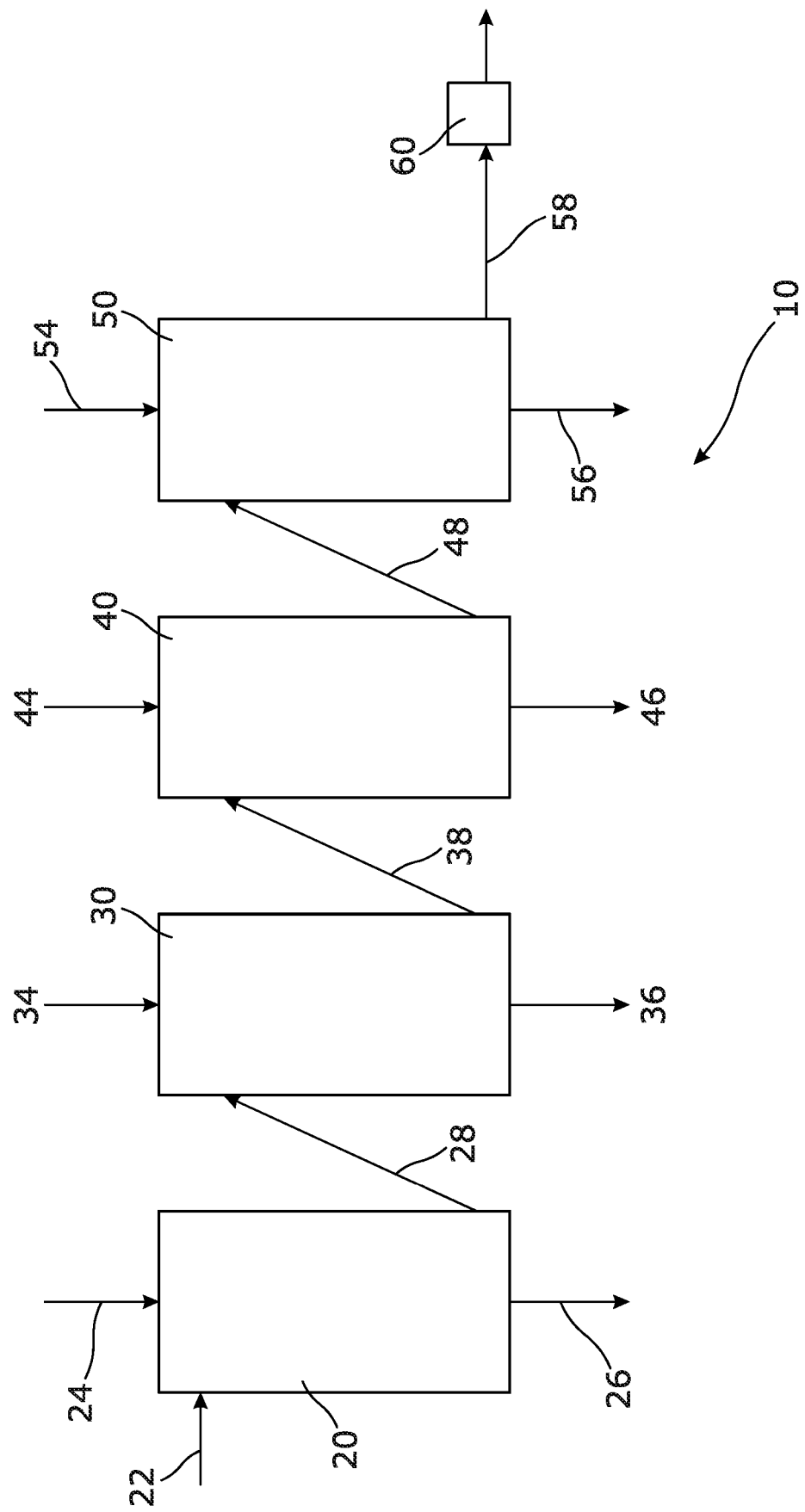
FIG. 1 shows a schematic diagram of a scrubbing train for performing a method in accordance with the present invention.

An embodiment of the present invention is shown in FIG. 1, which shows a scrubbing train 10 for treating the crude product of a dehydrohalogenation reaction. The crude product contains HFO-1234ze, though the scrubbing train may also be utilised in the production of other hydro(chloro) fluoroolefins such as HFO-1234yf, HCFO-1233zd, HFO-1233xf, HFO-1132a and HFO-1336mzz. The crude product stream, in addition to HFO-1234ze, also contains HF and/or HCl, as has been produced by the dehydrohalogenation, unreacted starting materials such as 1,1,1,3,3-pentafluoropropane (HFC-245fa) and/or 1-chloro-1,3,3,3-tetrafluoropropane (HCFC-244fa), together with other organic materials, such as those produced as by-products of the dehydrohalogenation reaction.

In brief, the crude product stream is passed into a first scrubbing column 20 through a feed line 22, while water is supplied to the scrubbing column 20 through scrubbing line 24. The scrubbing line 24 provides a mass flow of water sufficient to produce an effluent flow which has a HF concentration of around 5 wt %. The bulk of the HF and/or HCl present in the crude product stream is dissolved or otherwise absorbed in the water in the scrubbing column 20 to produce a first spent stream of aqueous HF and/or HCl, which is passed from the scrubbing column 20 through a first effluent line 26. A first treated product stream, having substantially reduced HF and/or HCl content, exits the first scrubbing column 20 through a second feed line 28 to be passed to a second scrubbing column 30.

In the second scrubbing column 30, the first treated product stream is contacted with a supply of aqueous caustic material, for example aqueous KOH, which is supplied to the scrubbing column 30 through a second scrubbing line 34. The concentration of the preferred aqueous KOH may be around 20 wt %. The aqueous caustic material reacts with remaining traces of HF and/or HCl in the treated product stream to produce a spent caustic stream which passes from the scrubbing column 30 through a second effluent line 36. A second treated product stream is passed from the second scrubbing column 30 through a third feed line 38 to a third scrubbing column 40.

The third scrubbing column 40, is adapted to remove water introduced to the second treated product stream during treatment in the first and second scrubbing columns 20, 30. In the third scrubbing column the second treated product stream is contacted with a supply of aqueous sulphuric acid at a concentration of around 78 wt % to around 90 wt %, which is supplied to the scrubbing column 40 through a third scrubbing line 44. The aqueous sulphuric acid acts to remove a portion of the water present in the second treated product stream, while the concentration of the sulphuric acid is sufficiently low to reduce the risk of significant degradation of the desired end product of HFO-1234ze. The spent aqueous sulphuric acid is removed from the third scrubbing column 40 through a third effluent line 46, while a third treated product stream is passed from the third scrubbing column 40 through a third feed line 48 to a fourth scrubbing column 50.

The fourth scrubbing column 50 provides for the further removal of water from the third treated product stream. In the fourth scrubbing column 50 the third treated product stream is contacted with a supply of aqueous sulphuric acid at a concentration of around 90 wt % to around 98 wt %, most preferably around 90 wt %, which is supplied to the scrubbing column 50 through a third scrubbing line 54. The aqueous sulphuric acid acts to provide a high degree of removal of the remaining water present in the third treated product stream. The relatively high concentration of sulphuric acid ensures that the rate of removal of water is higher than in the third scrubbing column 30, however lower starting concentration of water in the third treated product stream compared to the second product stream allows for a lower contact time and/or volume of acid, thereby reducing the risk of significant degradation of the desired end product of HFO-1234ze. The spent aqueous sulphuric acid is removed from the fourth scrubbing column 50 through a fourth effluent line 56, while a fourth treated product stream is passed from the fourth scrubbing column 50 through a fourth feed line 48 to a polishing bed 60.

The polishing bed 60 comprises an adsorbent material such as Sofnolime® soda lime or a molecular sieve such as a zeolite having a pore diameter in the region of 2 Å to 6 Å. The polishing bed removes any residual water, acids and impurities from the fourth treated product stream. The resulting product stream may be subjected to further distillation.

All effluent streams 26, 36, 46, 56 may be disposed of or be sent to recovery to ensure further use of any commercially valuable components, such as HF and/or HCl and/or any organic components they may contain. However, in some embodiments, the effluent stream 56 of the fourth scrubbing column 50 may be recycled by supplying it to the third scrubbing line 30 for use in the third scrubbing column 40.

In some embodiments, the first scrubbing column 20 may be replaced by one or more columns where the scrubbing fluid comprises aqueous HF, for example in a concentration around 50 wt %. In such embodiments, the concentration of HF in the effluent fluid would be expected to be greater than that of the scrubbing fluid and allows effective recovery of HF therefrom, for example by absorbing the HF into the scrubbing liquid to increase the HF concentration to around 70 wt %, followed by distillation of the around 70 wt % HF into a stream of essentially anhydrous HF that can be recovered for use in other processes and a stream comprising around 50 wt % HF which can be returned to the column replacing column 20.

REFERENCE EXAMPLES

Batchwise experiments were performed in 100 ml Hastelloy autoclaves with 30 ml sulphuric acid of varying concentrations. After evacuating the headspace, the reaction vessels were then charged with HFO-1234zeE to reach a pressure of 1.0 barg (approx. 1.2 g HFO-1234zeE). The autoclaves were submerged in a water bath at varied temperatures and stirred at 500 rpm for varying periods of time, all as shown in Table 1.

Fluoride Measurements

The spent liquor from each autoclave was tested for its fluoride content by use of an ion selective electrode. Prior to measurement, the solutions were adjusted to pH 5.5 with buffer solution. The original sulphuric acid solution did not contain any fluoride. The results are shown in Table 1.

Total Organic Carbon Measurement

The spent liquor from each autoclave was also tested for its total organic carbon (TOC) content before and after sparging with compressed air for 30 minutes. The original sulphuric acid solution did not contain any organic carbon. The results are shown in Table 1.

TABLE 1

| Example | Temp (° C.) | [$H_2SO_4$] (wt %) | Time (min) | F (ppm) | TOC pre sparge (ppm) | TOC post sparge (ppm) |
|---|---|---|---|---|---|---|
| 1 | 50 | 98 | 70.2 | 3020 | 1800 | 1555 |
| 2 | 40 | 98 | 120 | 1260 | 1355 | 880 |
| 3 | 60 | 98 | 360 | 13700 | 9805 | 9790 |
| 4 | 50 | 98 | 240 | 8063 | 4500 | 4515 |
| 5 | 35.9 | 98 | 240 | 1505 | 750 | 770 |
| 6 | 50 | 98 | 240 | 3685 | 3625 | 3695 |
| 7 | 40 | 98 | 360 | 4450 | 1980 | 2060 |
| 8 | 60 | 98 | 120 | 2540 | 3900 | 3350 |
| 9 | 50 | 98 | 240 | 3700 | 2830 | 3245 |
| 10 | 64.1 | 98 | 240 | 19050 | 10145 | 9910 |
| 11 | 50 | 98 | 408 | 10938 | 5175 | 5165 |
| 12 | 50 | 98 | 240 | 6750 | 2985 | 2895 |
| 13 | 50 | 98 | 240 | 4610 | 3685 | 3565 |
| 14 | 50 | 98 | 50 | 645 | 1135 | 880 |
| 15 | 40 | 98 | 240 | 2000 | 2670 | 2275 |
| 16 | 40 | 98 | 240 | 620 | 3720 | 1280 |
| 17 | 30 | 88 | 17.6 | 22 | 34 | |
| 18 | 30 | 78 | 30 | 14.08 | 16 | |
| 19 | 30 | 98 | 30 | 120 | 995 | |
| 20 | 30 | 88 | 60 | 14.36 | 41 | |
| 21 | 30 | 88 | 60 | 8.58 | 65 | |
| 22 | 30 | 98 | 90 | 314 | 630 | |
| 23 | 30 | 88 | 60 | 15.48 | 37 | |
| 24 | 30 | 78 | 90 | 9.52 | 13 | |
| 25 | 30 | 102.1 | 60 | 402 | 855 | |
| 26 | 30 | 88 | 102.4 | 13.32 | 37 | |
| 27 | 30 | 88 | 60 | 11.84 | 40 | |
| 28 | 30 | 73.9 | 60 | 5.48 | 14 | |
| 29 | 30 | 88 | 60 | 10.2 | 33 | |

The results were plotted into a series of response surface plots as shown in FIGS. 2 to 5.

Figure 2:
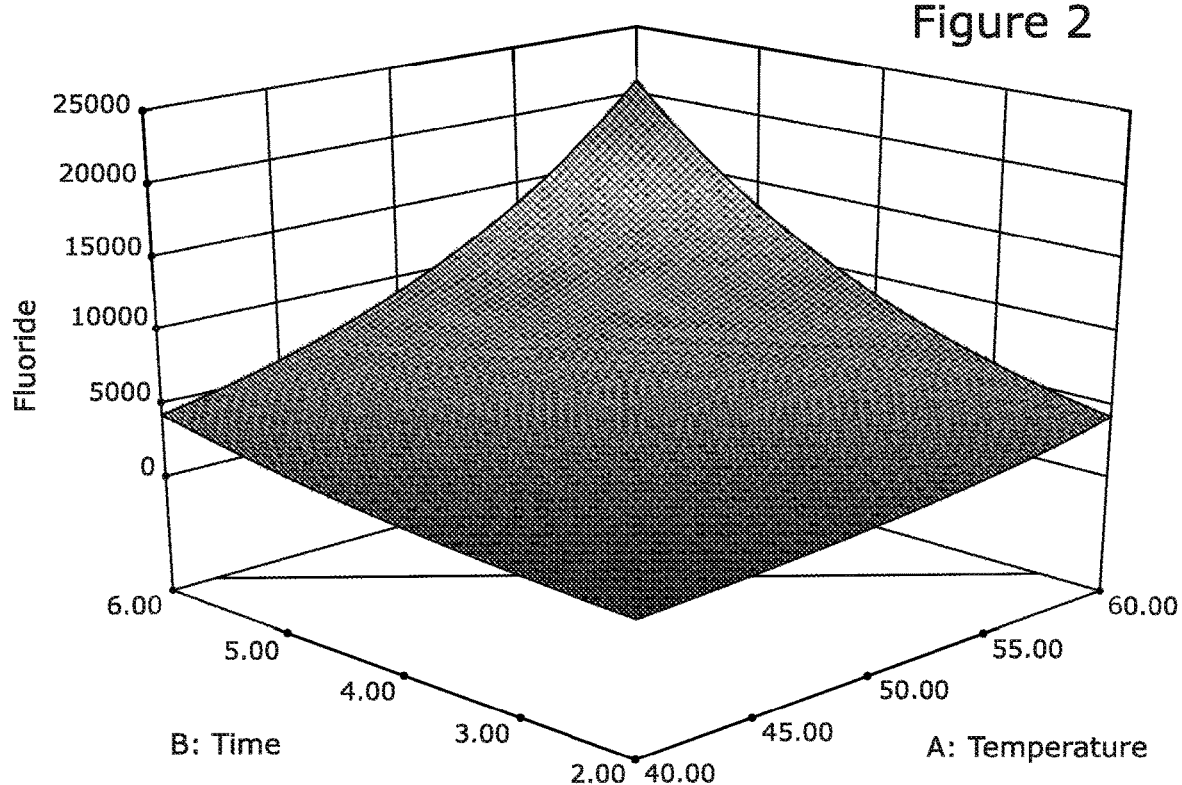
FIGS. 2 to 7 show response surface plots of fluoride and total organic carbon produced by contacting HFO-1234ze with sulphuric acid.

FIG. 2 shows the fluoride level versus temperature and contact time after reaction with HFO-1234zeE at a constant sulphuric acid concentration of 98 wt %. Increasing time and temperature each individually appear to increase the fluoride content in the spent solution, but the combination of both has the greatest influence, as shown by the upwards slope of the surface towards the highest temperatures and longest contact times in the far corner of the plot.

Figure 3:
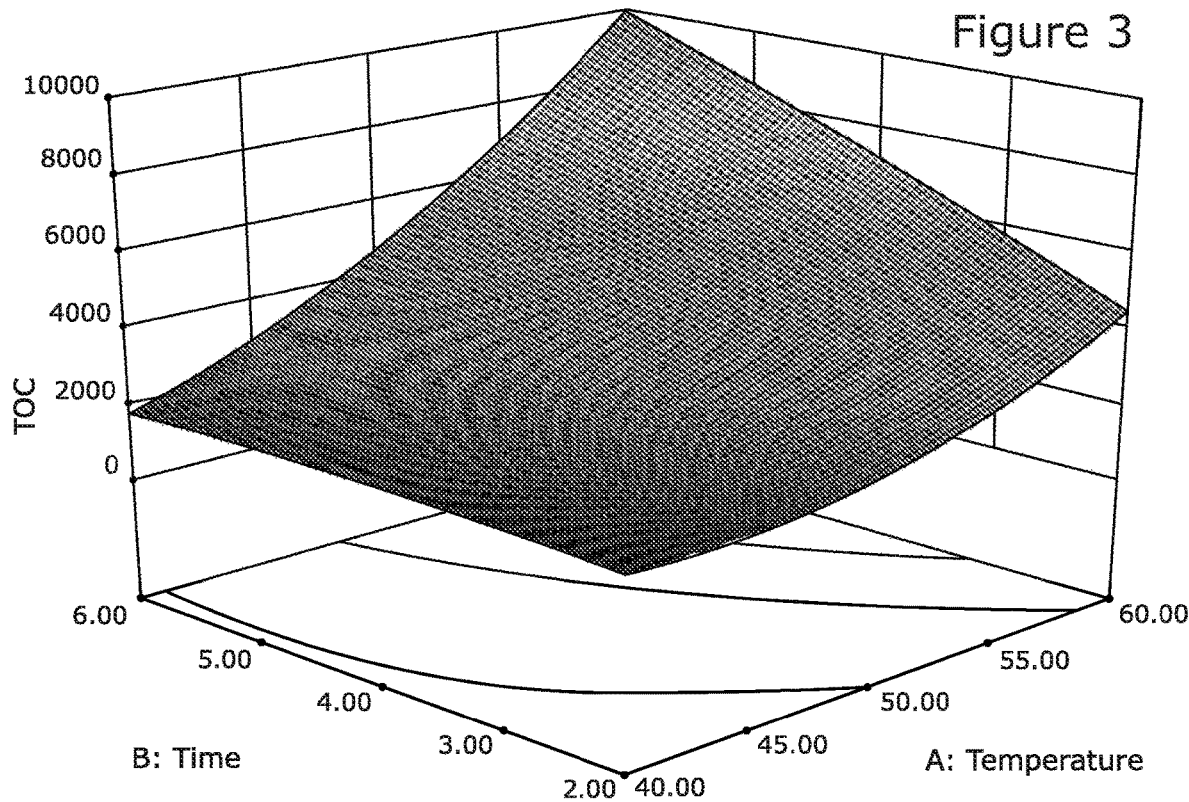

FIG. 3 shows the TOC levels measured at different temperatures and contact times of $H_2SO_4$ at a concentration of 98 wt % with HFO-1234zeE. Again, increasing temperature and time each individually increase the TOC content, but the combination of both has the greatest influence. The overall TOC levels appear high, indicating a relatively severe reaction of the organic with $H_2SO_4$.

The sparging of a sample of each solution with air was designed to remove any medium to low boilers produced as a result of decomposition, and highlight an option for treatment of the solutions prior to disposal. The results however, show no statistical difference within the 95% confidence limits between samples before and after sparging.

Figure 4:
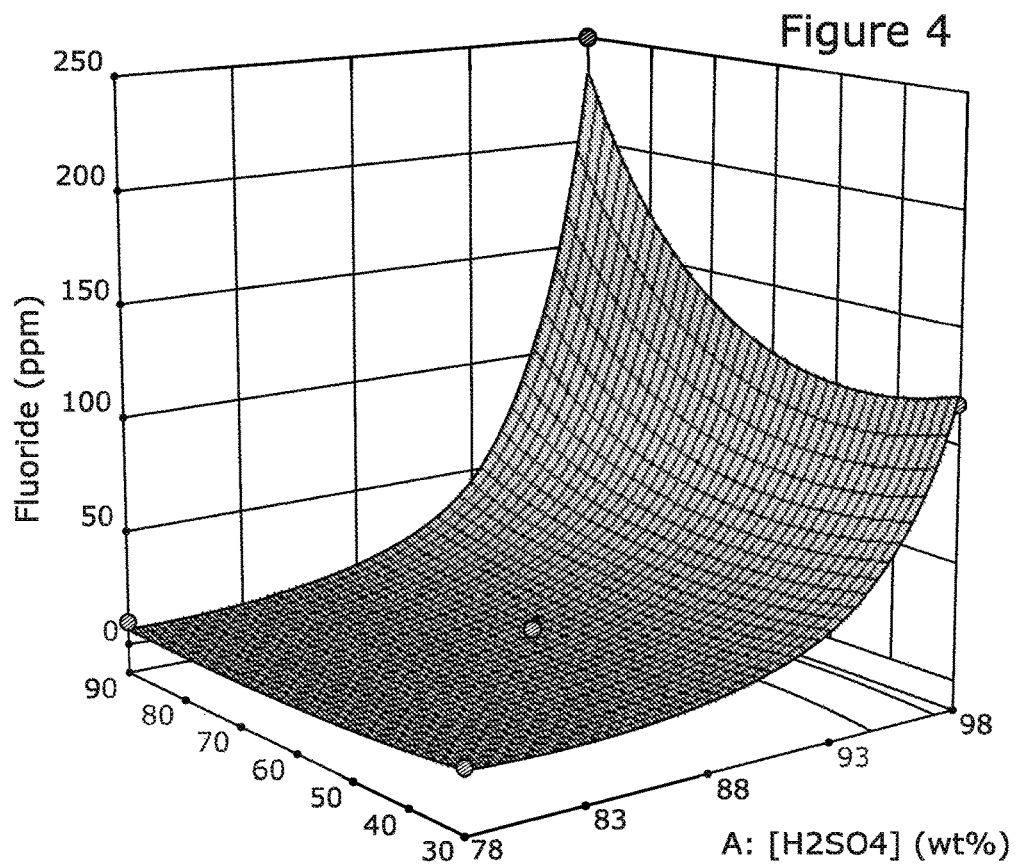
Figure 5:
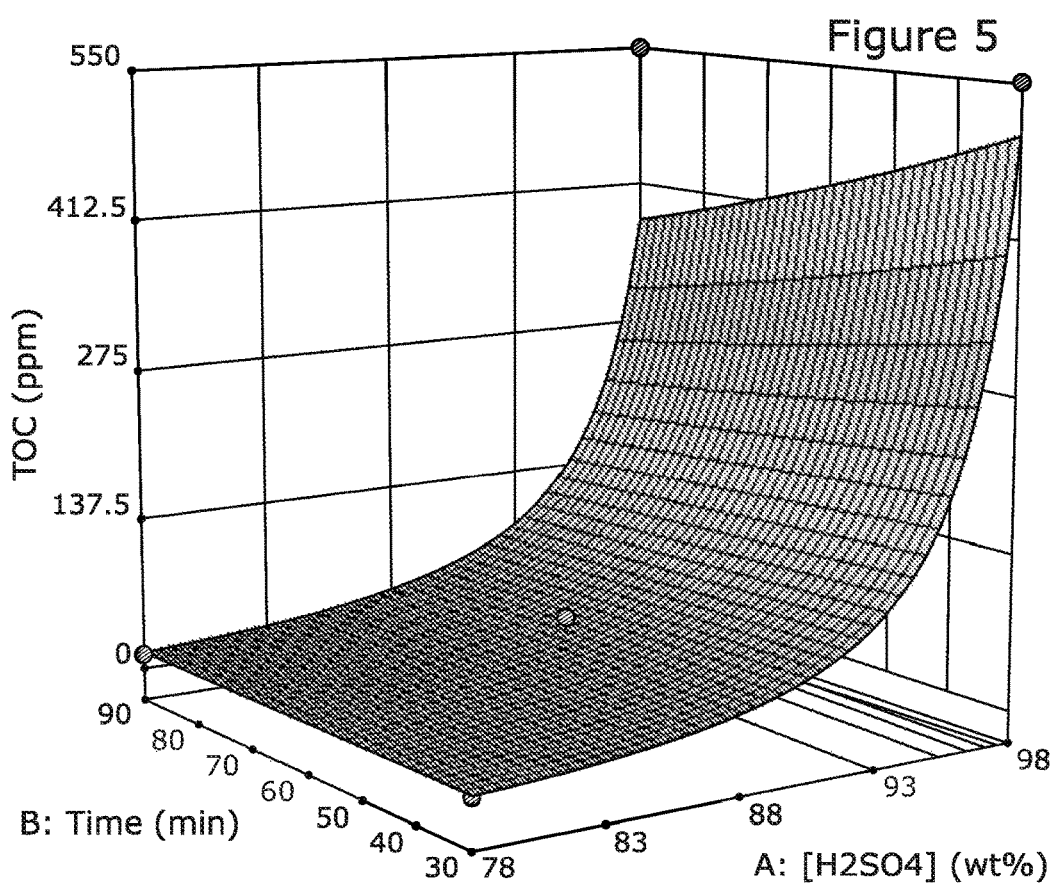

A response surface plot in FIG. 4 shows how the fluoride content remaining in solution changes with contact time and the concentration of sulphuric acid between 78 wt % and 98 wt % at a constant temperature of 30° C. At low sulphuric acid concentration and short contact times, there are only very low levels of fluoride, which increase very slowly with increasing contact times and sulphuric acid concentration. As the sulphuric acid concentration approaches 98 wt %, the fluoride levels suddenly increase sharply, particularly at high contact times.

The TOC results (see FIG. 5) obtained for sulphuric acid concentration varying from 78 wt % to 98 wt % at a constant temperature of 30° C. show a similar trend to the fluoride results, in that there is very little TOC present at low sulphuric acid concentrations and short contact times, but as the concentration reaches 98 wt %, the TOC levels appear to rise rapidly, regardless of contact time.

Further experiments were conducted to investigate the effect of sulphuric acid concentrations in excess of 90 wt % on the stability of the HFO-1234zeE, the results of which are shown in Table 2. No investigation of TOC was performed in these experiments.

TABLE 2

| Example | Temp (° C.) | Time (min) | [$H_2SO_4$] (wt %) | F (ppm) |
|---|---|---|---|---|
| 30 | 30 | 90 | 90 | 33.2 |
| 31 | 30 | 30 | 98 | 98.8 |
| 32 | 30 | 60 | 99.7 | 160.6 |
| 33 | 30 | 60 | 94 | 63.6 |
| 34 | 30 | 60 | 88.3 | 8 |
| 35 | 30 | 30 | 90 | 38.3 |
| 36 | 30 | 17.6 | 94 | 25.4 |
| 37 | 30 | 102.4 | 94 | 64 |
| 38 | 30 | 60 | 94 | 57.4 |
| 39 | 30 | 60 | 94 | 56.4 |
| 40 | 30 | 60 | 94 | 57.6 |
| 41 | 30 | 60 | 94 | 43 |
| 42 | 30 | 90 | 98 | 316 |
| 43 | 30 | 30 | 94 | 37.4 |
| 44 | 30 | 60 | 96 | 66.4 |
| 45 | 30 | 60 | 93.2 | 15.2 |
| 46 | 30 | 17.6 | 96 | 25.2 |
| 47 | 30 | 30 | 98 | 56.6 |
| 48 | 30 | 102.4 | 96 | 144.4 |
| 49 | 30 | 90 | 94 | 76.4 |
| 50 | 30 | 90 | 98 | 141.2 |
| 51 | 30 | 60 | 96 | 69.4 |
| 52 | 30 | 60 | 96 | 72 |
| 53 | 30 | 60 | 98.8 | 165.6 |
| 54 | 30 | 60 | 96 | 68.4 |
| 55 | 30 | 60 | 96 | 77 |

Figure 6:
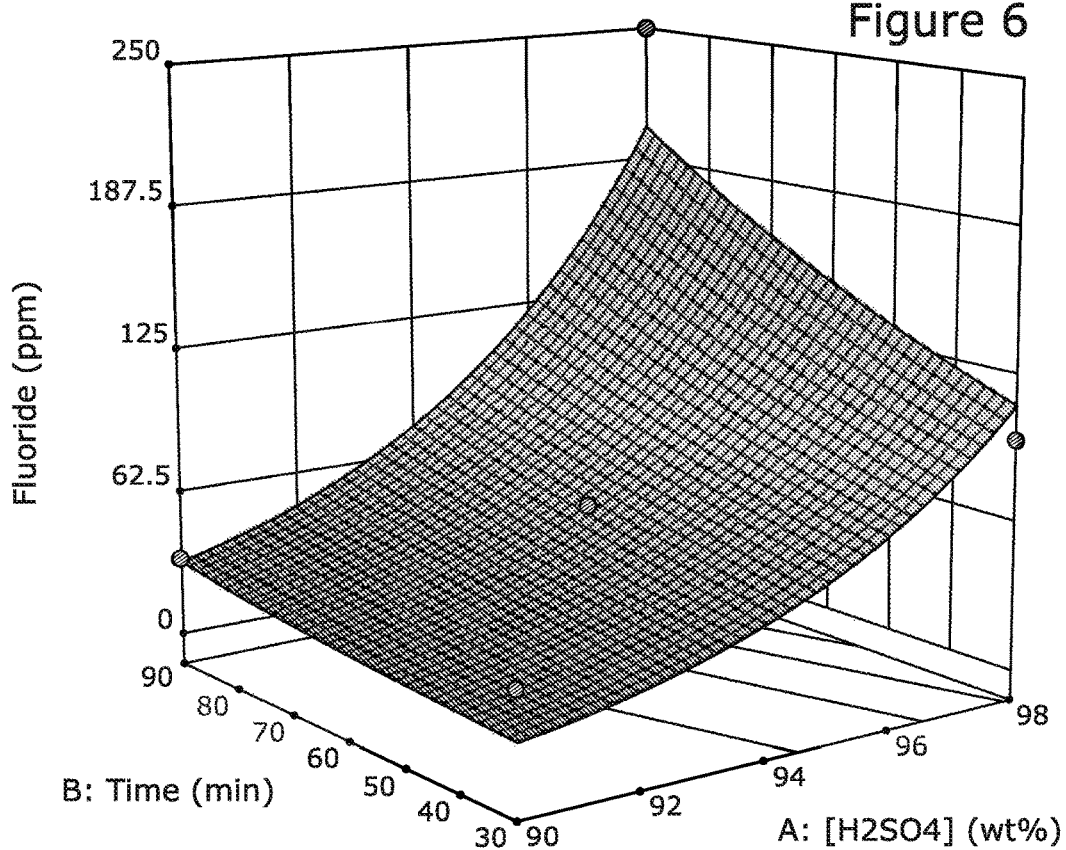
Figure 7:
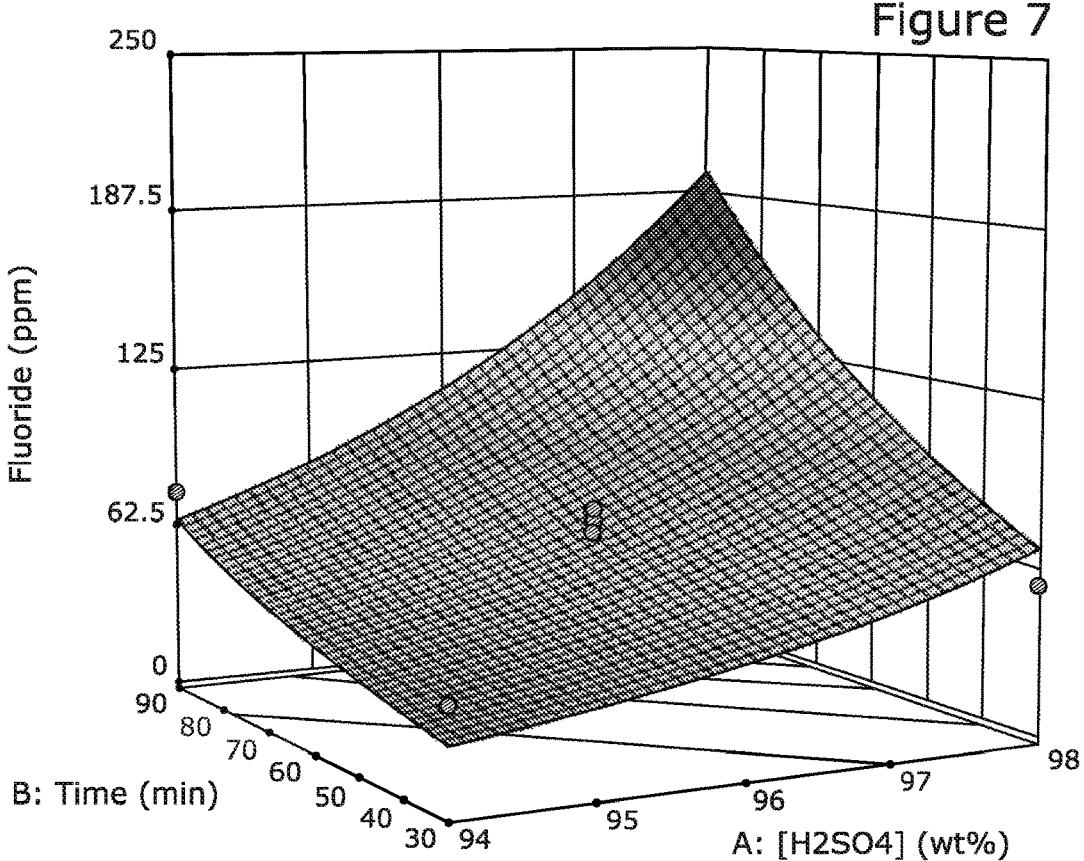

FIG. 6 shows a response surface plot of fluoride concentrations against sulphuric acid concentration between 90 wt % and 98 wt % at a constant temperature of 30° C. As can be seen, there is a gradual increase in fluoride with increasing contact time and sulphuric acid concentrations. There appear to be acceptably low levels of fluoride at the lower concentrations. FIG. 7 shows a similar plot focussed on sulphuric acid concentrations between 94 wt % and 98 wt %.

The concentration of water in HFO-1234zeE is a function of the concentration of sulphuric acid with which it contacts and the efficiency of the scrubber. Data demonstrating the partial pressure of water above sulphuric acid solutions of varying concentrations can be used to determine the equilibrium concentration. This data suggests that the concentration of sulphuric acid provided to the final (or only) sulphuric acid scrubber should be above 80 wt % to achieve a concentration of water in HFO-1234zeE below 100 ppm. The present results show that at 94 wt % sulphuric acid the fluoride levels range from 37-76 ppm over the different contact times. As the sulphuric acid concentration is increased from 94 wt %, the fluoride concentration in the spent sulphuric acid quickly starts to rise. It thus appears that an optimum sulphuric acid concentration for drying hydro(chloro)fluoroolefins such as HFO-1234ze would be between about 90 wt % and about 94 wt %. As can also be seen from the results presented above, concentrations of sulphuric acid below 90 wt %, for example between 78 wt % and 90 wt %, provide manageable levels of fluoride and TOC (and thus product degradation) and as such concentrations in that range are considered optimal for the first of two sulphuric acid drying stages. As can also be seen from the results presented above, concentrations of sulphuric acid below 90 wt %, for example between 78 wt % and 90 wt %, provide manageable levels of fluoride and TOC (and thus product degradation) and as such concentrations in that range have been found to be optimal for the first of two sulphuric acid drying stages.

Reference Example 56

A further experiment was performed using 30 mL of 94 wt % $H_2SO_4$ warmed to 30° C. and stirred at 500 rpm. After evacuating the headspace the autoclave was charged to 2.0 barg with HFO-1234yf (1.2 g) and reacted for 60 min before analysing the spent $H_2SO_4$ liquors for fluoride concentration. The spent sulphuric acid solution contained no detectable fluoride.

Example 57

Drying of hydrofluoroolefins with high and reduced concentrations of sulphuric acid.

300 g of either HFO-1234ze(E) or HFO-1234yf was added to a 500 mL Whitey bomb and doped with ~300 ppm of water. The moisture content of the composition was analysed before and after the addition of the water. 30 g of the wet hydrofluoroolefin was added to a Whitey bomb containing 50 mL of sulphuric acid (at a concentration of either 98 wt % (aq) or 80 wt % (aq)) and shaken for 10 minutes. The dried hydrofluoroolefin was subsequently isolated from the Whitey bomb at 10° C. and analysed for moisture content. The results of drying with 98 wt % $H_2SO_4$ (aq) are presented in Tables 3 and the results of drying 80 wt % $H_2SO_4$ (aq) are presented in Table 4.

TABLE 3

| HFO | Moisture of starting material (ppm) | | Moisture after doping with $H_2O$ (ppm) | | Moisture after drying (ppm) | |
| --- | --- | --- | --- | --- | --- | --- |
|  | Run 1 | Run 2 | Run 1 | Run 2 | Run 1 | Run 2 |
| 1234ze(E) | 27 | 27 | 233.9 | 239.6 | 67.9 | 60.6 |
| 1234yf | 127.2 | 126.9 | 250 | 290 | 73.6 | 73.9 |

TABLE 4

| HFO | Moisture of starting material (ppm) | | Moisture after doping with $H_2O$ (ppm) | | Moisture after drying (ppm) | |
| --- | --- | --- | --- | --- | --- | --- |
|  | Run 1 | Run 2 | Run 1 | Run 2 | Run 1 | Run 2 |
| 1234ze(E) | 27 | 27 | 290 | 301 | 56.7 | 66.50 |
| 1234yf | 127.2 | 126.9 | 250 | 290 | 63 | 52.3 |

It is clear from this direct comparison that the drying performance of sulphuric acid remains sufficiently high at a lower concentration for a range of hydrofluoroolefins. The high performance at a reduced concentration results in reduced degradation of the desired hydrofluoroolefin and thus greater final product yields. The reduced concentration of sulphuric acid also reduces the concentration of potentially hazardous organic material in the spent sulphuric acid stream.

Example 58

A water containing sample of (E)-1234ze was dried [by agitating] at 60° C. in [contact with] a scrubbing medium comprising 98% wt sulphuric acid. The mixture was then neutralised and extracted with a solvent. The solvent extract was dried, filtered and concentrated. Samples of the concentrated extract were taken and analysed by 1-D NMR ($^1H$, $^{13}C$ and $^{19}F$), 2-D NMR ($^1H$-$^1H$ COSY and $^1H$-$^{13}C$ HSQC), gas chromatography and ISE to identify the decomposition products and pathways.

Several decomposition products were identified in the spent scrubbing solution, including fluoracrylic acid, polyfluoracrylic acid, formic acid and fluoroformaldehyde, together with several unsaturated fluorine containing oligomers.

Preferences and options for a given aspect, feature or parameter of the invention should, unless the context indicates otherwise, be regarded as having been disclosed in combination with any and all preferences and options for all other aspects, features and parameters of the invention.

Where a molecule, for example HFO-1234ze, may take the form of E and Z isomers, the general disclosure of that molecule is intended to refer equally to both the E and Z isomers.

The invention claimed is:
1. A method for purifying a fluid comprising a first drying stage which comprises contacting a first fluid stream comprising one or more hydro(chloro)fluoroolefins and water with a source of sulphuric acid at a concentration between 75 wt % and 95 wt % to produce a first treated fluid stream comprising the hydro(chloro)fluoroolefin(s) and a first spent sulphuric acid stream, wherein the first treated fluid stream comprises a lower concentration of water than the first fluid stream.
2. A method comprising an integrated process for producing one or more hydro(chloro)fluoroolefins comprising:
   dehydrohalogenating one or more hydro(chloro)fluoroalkanes to form a crude product stream;
   subjecting the crude product stream to a first acid removal step comprising contacting the crude product stream with water or a source of aqueous acid to produce a treated product stream and a spent aqueous acid stream;
   subjecting the treated product stream to a second acid removal step comprising contacting the treated product stream with a source of aqueous alkali to produce a second treated product stream and a spent aqueous alkali stream;

subjecting the second treated product stream, in the form of a first fluid stream, to a first drying stage comprising contacting the first fluid stream with a source of sulphuric acid at a concentration between 75 wt % and 95 wt % to produce a first treated fluid stream comprising the hydro(chloro)fluoroolefin(s) and a first spent sulphuric acid stream.

3. The method according to claim 1, wherein the first treated fluid stream comprises less than 1 wt % water.

4. The method according to claim 1, wherein the first fluid stream comprises less than 20 wt % HF.

5. The method according to claim 1, wherein the first fluid stream comprises less than 20 wt % HCl.

6. The method according claim 1, wherein at least 50 wt % of the first fluid stream comprises the hydro(chloro) fluoroolefin(s).

7. The method according to claim 6, wherein at least 50 wt % of the first fluid stream comprises a hydro(chloro)fluoroolefin selected from the group consisting of hydrofluoropropenes, hydrochlorofluoropropenes, hydrofluoroethylenes, hydrofluorobutenes and hydrochlorofluorobutenes.

8. The method according claim 1, wherein the hydro(chloro)fluoroolefins include one or more of HFO-1234yf, HFO-1234ze, 1-chloro-3,3,3-trifluoropropene (HCFO-1233zd), 2-chloro-3,3,3-trifluoropropene (HCFO-1233xf), 1,1,1-4,4,4-hexafluoro-but-2-ene (HFO-1336mzz) and 1,1-difluoroethylene (HFO-1132a).

9. The method according to claim 1, wherein the first fluid stream is contacted with the source of sulphuric acid at a temperature between 10° C. and 70° C.

10. The method according to claim 1, wherein the first spent sulphuric stream comprises less than 20000 ppm fluoride.

11. The method according to claim 1, wherein the first spent sulphuric stream comprises less than 10000 ppm total organic carbon.

12. The method according to claim 1, wherein the first spent sulphuric stream comprises one or more compounds selected from fluoracrylic acid, polyfluoracrylic acid, formic acid and fluoroformaldehyde, and/or one or more unsaturated fluorine containing oligomers.

13. The method according to claim 1, wherein the method comprises a second drying step comprising contacting the first treated fluid stream with a second source of sulphuric acid to produce a second treated fluid stream comprising the hydro(chloro)fluoroolefin(s) and a second spent sulphuric acid stream, wherein the second treated fluid stream comprises a lower concentration of water than the fluid stream.

14. The method according to claim 13, wherein the first source of sulphuric acid comprises aqueous sulphuric acid in a concentration between 78 wt % and 90 wt %.

15. The method according to claim 13, wherein the second treated fluid stream comprises less than 500 ppm water.

16. The method according to claim 15, wherein the second source of sulphuric acid comprises aqueous sulphuric acid at a concentration between 60 wt % and 98 wt %.

17. The method according to claim 13, wherein the first treated fluid stream is contacted with the second source of sulphuric acid at a temperature between 10° C. and 70° C.

18. The method according to claim 13, wherein the second spent sulphuric stream comprises less than 20000 ppm fluoride.

19. The method according to claim 13, wherein the second spent sulphuric stream comprises less than 10000 ppm total organic carbon.

20. The method according to claim 13 wherein the second spent sulphuric stream comprises one or more compounds selected from fluoracrylic acid, polyfluoracrylic acid, formic acid and fluoroformaldehyde, and/or one or more unsaturated fluorine containing oligomers.

21. The method according claim 1, wherein the first and/or, if produced, second treated fluid stream(s) comprise the hydro(chloro)fluoroolefins in a purity of at least 99 wt %.

22. The method according to claim 1, wherein the first and/or, if produced, second treated fluid stream is contacted with an adsorbent material.

23. The method according to claim 22, wherein the adsorbent material comprises soda lime and/or one or more molecular sieves, for example one or more zeolites having pores sizes in the region of 2 Å to 10 Å.

24. The method according to claim 1, wherein the first treated fluid stream, is subjected to distillation to separate some or all of the remaining components.

25. The method according to claim 1 further comprising a preceding acid removal step which preferably comprises the treatment of a crude product stream to remove at least a portion of any HF and/or HCl in the crude product stream to provide the first fluid stream.

26. The method according to claim 1, wherein the crude product stream is the product stream of a dehydrohalogenation reaction.

27. The method according to claim 1, wherein the acid removal step comprises contacting the crude product stream with water to produce a spent stream of aqueous acid and a treated product stream, the treated product stream having a lower acid concentration than the crude product stream.

28. The method according to claim 1, wherein the acid removal step comprises contacting the crude product stream with a source of aqueous acid to produce a spent stream of aqueous acid and a treated product stream, the treated product stream having a lower acid concentration than the crude product stream.

29. The method according to claim 28, wherein the source of aqueous acid comprises aqueous HF a concentration between 30 wt % and 60 wt %.

30. The method according to claim 2, wherein the treated product stream is provided directly to the first drying stage, in the form of the first fluid stream.

31. The method according to claim 2, wherein the treated product stream is subjected to one or more further treatment steps before being provided to the first drying stage.

32. The method according to claim 29, wherein the treated product stream is subjected to a second acid removal step.

33. The method according to claim 32, wherein the source of aqueous alkali comprises an aqueous caustic solution.

34. The method according to claim 32, wherein the second treated product stream is provided directly to the first drying stage.

35. The method according to claim 5, wherein the first fluid stream comprises less than 1 wt % HF.

36. The method according to claim 35, wherein the wherein the first fluid stream comprises no more than trace quantities of HF.

37. The method according to claim 7, wherein at least 80 wt % of the first fluid stream comprises said hydro(chloro)fluoroolefins.

38. The method according to claim 10 wherein the first spent sulphuric stream comprises less than 1000 ppm fluoride.

39. The method according to claim 10 wherein the first spent sulphuric stream comprises less than 25 ppm fluoride.

40. The method according to claim 11 wherein the first spent sulphuric stream comprises less than 1000 ppm organic carbon.

41. The method according to claim 11 wherein the first spent sulphuric stream comprises less than 25 ppm total organic carbon.

42. The method according to claim 15 wherein the second treated fluid stream comprises less than 10 ppm water.

43. The method according to claim 16 wherein the second source of sulphuric acid comprises aqueous sulphuric acid at a concentration between 90 wt % and 94 wt %.

44. The method according to claim 13, wherein the first treated fluid stream is contacted with the second source of sulphuric acid at a temperature between 25° C. and 35° C.

45. The method according to claim 18 wherein the second spent sulphuric stream comprises less than 1000 ppm fluoride.

46. The method according to claim 44 wherein the second spent sulphuric stream comprises less than 25 ppm fluoride.

47. The method according to claim 19 wherein the second spent sulphuric stream comprises less than 25 ppm total organic carbon.

48. The method according to claim 21, wherein the first and/or, if produced, second treated fluid stream(s) comprise the hydro(chloro)fluoroolefins in a purity of at least 99.9 wt %.

49. The method according to claim 22, wherein one or more molecular sieves having pore sizes in the region of 3 Å to 6 Å.

50. The method according to claim 32, wherein the second acid removal step comprises contacting the treated product stream with an aqueous alkali to produce a second treated product stream and a spent aqueous alkali stream, the second treated product stream having a lower acid concentration than the treated product stream.

51. The method according to claim 32, wherein the source of aqueous alkali comprises NaOH or KOH.

52. The method according to claim 50, wherein the concentration of NaOH or KOH is less than 5 wt %.

\* \* \* \* \*